(12) United States Patent  (10) Patent No.: US 6,471,661 B1
Burns  (45) Date of Patent: Oct. 29, 2002

(54) TOOL FOR MEASURING THE CURVE OF THE CERVICAL SPINE AND ASSOCIATED METHODS

(76) Inventor: Robert J. Burns, 8215 Oak St., Yalaha, FL (US) 34797

( * ) Notice: Subject to any disclaimer, the term of this patent is extended or adjusted under 35 U.S.C. 154(b) by 0 days.

(21) Appl. No.: 09/494,343

(22) Filed: Jan. 28, 2000

(51) Int. Cl.[7] ................................................ A61B 5/00
(52) U.S. Cl. ........................... 600/594; 33/512; 602/18
(58) Field of Search .................................. 600/587, 594; 33/511, 572; 5/636, 844; 602/17, 18

(56) References Cited

U.S. PATENT DOCUMENTS

| | | | | |
|---|---|---|---|---|
| 5,018,531 A | * | 5/1991 | Hartman | 600/587 |
| 5,471,995 A | * | 12/1995 | Halliday | 600/587 |
| 5,542,910 A | * | 8/1996 | Oliver | 602/18 |
| 6,165,146 A | * | 12/2000 | Giebler | 602/18 |

FOREIGN PATENT DOCUMENTS

FR  2492-250  * 4/1982 ................. 600/594

* cited by examiner

*Primary Examiner*—Max Hindenburg
(74) *Attorney, Agent, or Firm*—Allen, Dyer, Doppelt, Milbrath & Gilchrist, P.A.

(57) ABSTRACT

An apparatus and methods for measuring and supporting the cervical curve include a tool comprising a plurality of predetermined curves each substantially complementary in shape to a cervical curve, for measuring a person's cervical curve when the tool is positioned adjacent the nape of the person's neck. The tool comprises a predetermined size range of curves for allowing measurement of variously sized cervical curves. An embodiment of the tool includes a plurality of cards having a predetermined curve positioned along the edge of the card, for positioning adjacent the nape of the person's neck to measure the cervical curve. The method includes providing a cervical support pillow having dimensions substantially corresponding to the cervical curve measurement.

11 Claims, 4 Drawing Sheets

TOOL FOR MEASURING THE CURVE OF THE CERVICAL SPINE AND ASSOCIATED METHODS

FIELD OF THE INVENTION

The present invention relates to the field of prevention of skeletal misalignments and, more particularly, to a tool and method for measuring the cervical curve of a person's neck and for providing proper support therefor while the person is lying down.

BACKGROUND OF THE INVENTION

Chinese and Egyptian records provide evidence that the theory that the human nervous system plays a critical part in maintaining the well-being of our bodies was developed in ancient times. Spinal manipulation was known as long ago as the year 2700 BC in China as a means of treating various maladies. Greek writings from about 1500 BC provide directions for manipulation of the legs in the treatment of lower back injuries. The records of other ancient cultures from North America, Babylon, Syria, Tibet, and Japan also indicate that soft tissue manipulation has also been practiced in the treatment of pain related to various conditions and disease. The modern health care specialty of chiropractic medicine is based upon this ancient idea.

Practitioners of chiropractic are known as chiropractors. They treat patients primarily for pain in the back, neck, and for chronic headaches. Chiropractors generally treat their patients by the application of pressure to the skeletal joints, both manually and by certain instruments. A primary focus of chiropractic treatment is the spinal column, since it is believed that the misalignment of vertebrae in the spine disrupts the function of the nervous system, in turn leading to imbalances and disease states which manifest through pain in various locations of the body. Consequently, a typical chiropractic adjustment involves realignment of the spine by manipulation of the vertebrae.

However, the typical chiropractic patient may have difficulty maintaining the spine in proper alignment following a chiropractic adjustment. It has been recognized that one cause of such difficulty is inappropriate positioning of the spine during the sleep, the result of inadequate support particularly for the neck area of the patient, also known as the cervical spine.

SUMMARY OF THE INVENTION

With the foregoing in mind, the present invention advantageously provides a tool for measuring a person's cervical curve and associated methods.

It is an object of the present invention to provide a tool to measure the curve of the cervical spine of a person, also referred to herein as the cervical curve.

It is another object of the invention to provide a simple, inexpensive, and easily portable tool for measuring the curvature of the cervical spine, or cervical curve.

It is a further object of the invention to provide a method for providing proper support for the cervical spine when the person lies down, such as during sleep, by measuring the cervical curve and providing a cervical support pillow correlated in dimension to the cervical curve.

In view of those objects, the tool comprises a plurality of predetermined curved portions each substantially complementary in shape to a cervical curve, for measuring a person's cervical curve when the tool is positioned adjacent the nape of the person's neck. The plurality of predetermined curves comprises a predetermined size range of curves to allow measurement of cervical curves in persons of varying size and stature.

In one embodiment of the invention, the tool comprises a plurality of cards, each card including a predetermined curve substantially complementary in shape to a cervical curve. The tool is used for measuring a person's cervical curve when at least one of the cards is positioned adjacent the nape of the person's neck. The plurality of cards comprises a predetermined size range of curves, with the curve positioned along an edge of the card in one embodiment of the invention.

An associated method includes the steps of measuring the cervical curve of a person, and selecting a cervical support pillow having dimensions substantially corresponding to the cervical curve measurement so that the pillow substantially supports the neck when the person is lying down.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION

The present invention will now be described more fully hereinafter with reference to the accompanying drawings, selecting an appropriately dimensioned cervical support pillow.

FIGS. 1 through 4 illustrate a tool 10 for measuring a person's cervical curve 12. The tool 10 comprises a plurality of predetermined curves 14 each substantially complementary in shape to a cervical curve 12. A person's cervical curve 12 is measured when the tool 10 is positioned adjacent the nape of the person's neck. Those skilled in the art will know that the cervical curve 12 is that generally curved portion of the back side of a person's neck from about the base of the skull to about the level of the shoulders, and that the nape of the neck is another name for the back of the neck.

Figure 1:
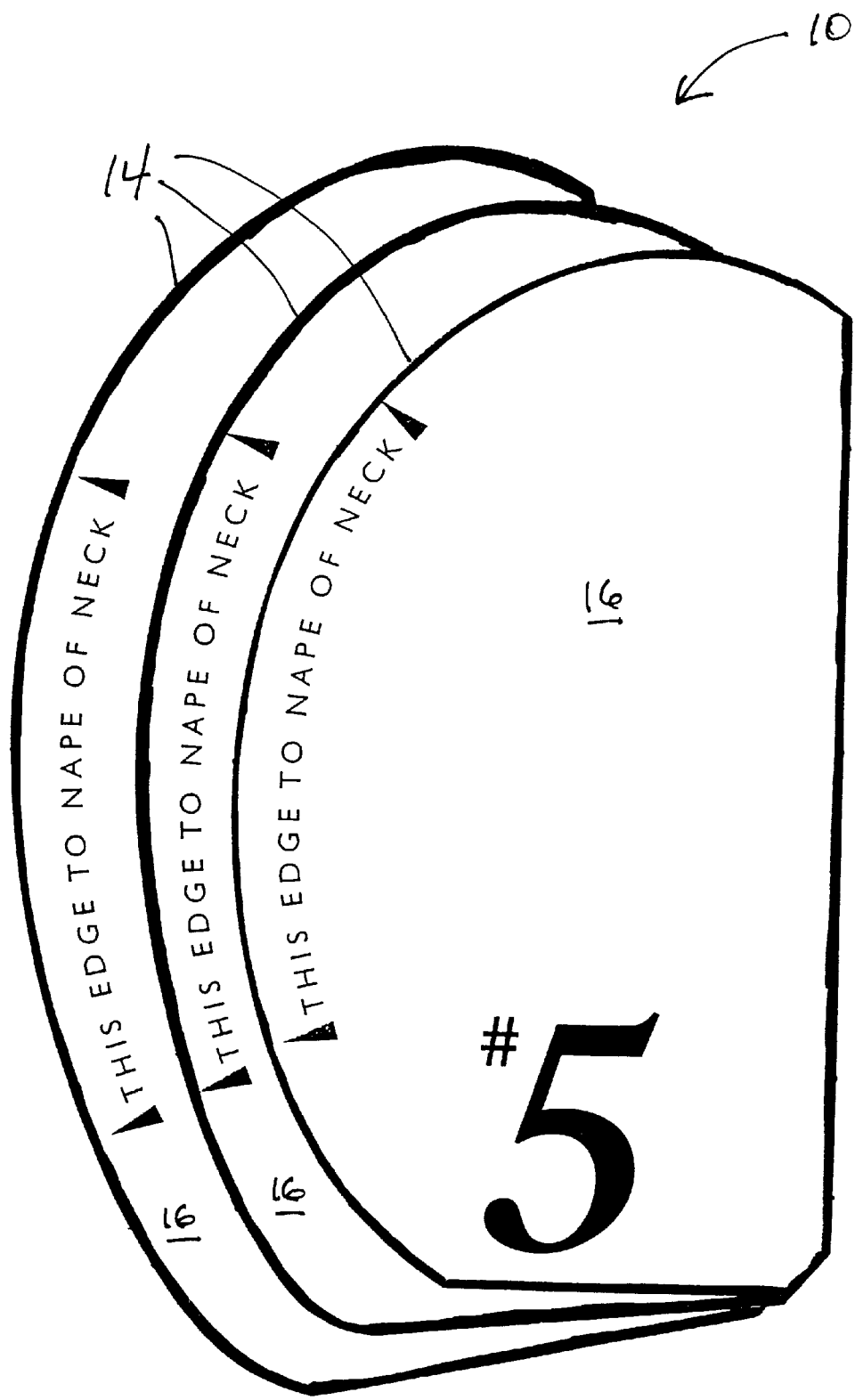
FIG. 1 is a perspective view of the tool according to an embodiment of the present invention.

In a preferred embodiment of the tool 10, as shown in use in FIG. 1, the plurality of predetermined curved portions 14 comprises a predetermined size range of curves.

Figure 3:
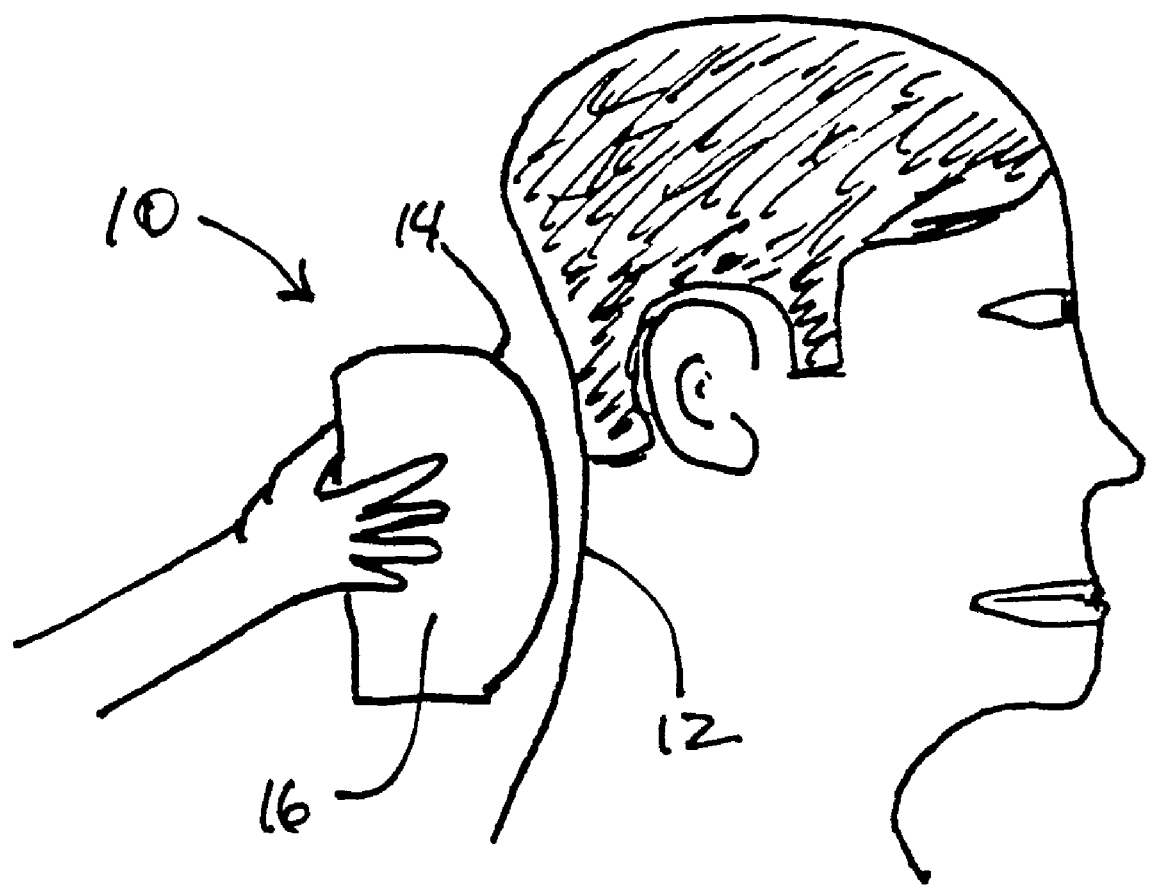
FIG. 3 is an environmental view of the tool in use for measuring the cervical curve of a person.

In another preferred embodiment the tool comprises a plurality of cards 16, as shown in FIG. 1. For convenience, the cards may be connected to each other, although this is not necessary. Each card 16 includes a predetermined curve 14 which is substantially complementary in shape to a cervical curve 12, as illustrated in FIG. 3. The complementary curve 14 allows for measuring a person's cervical curve 12 when at least one of the cards 16 is positioned adjacent the nape of the person's neck, as seen in FIG. 3. In addition, the plurality of cards may preferably include a predetermined size range of curves, which are useful for measuring variously sized cervical curves. In a preferred tool 10, at least one card of the plurality comprises the predetermined curve along an edge of the card.

Figure 4:
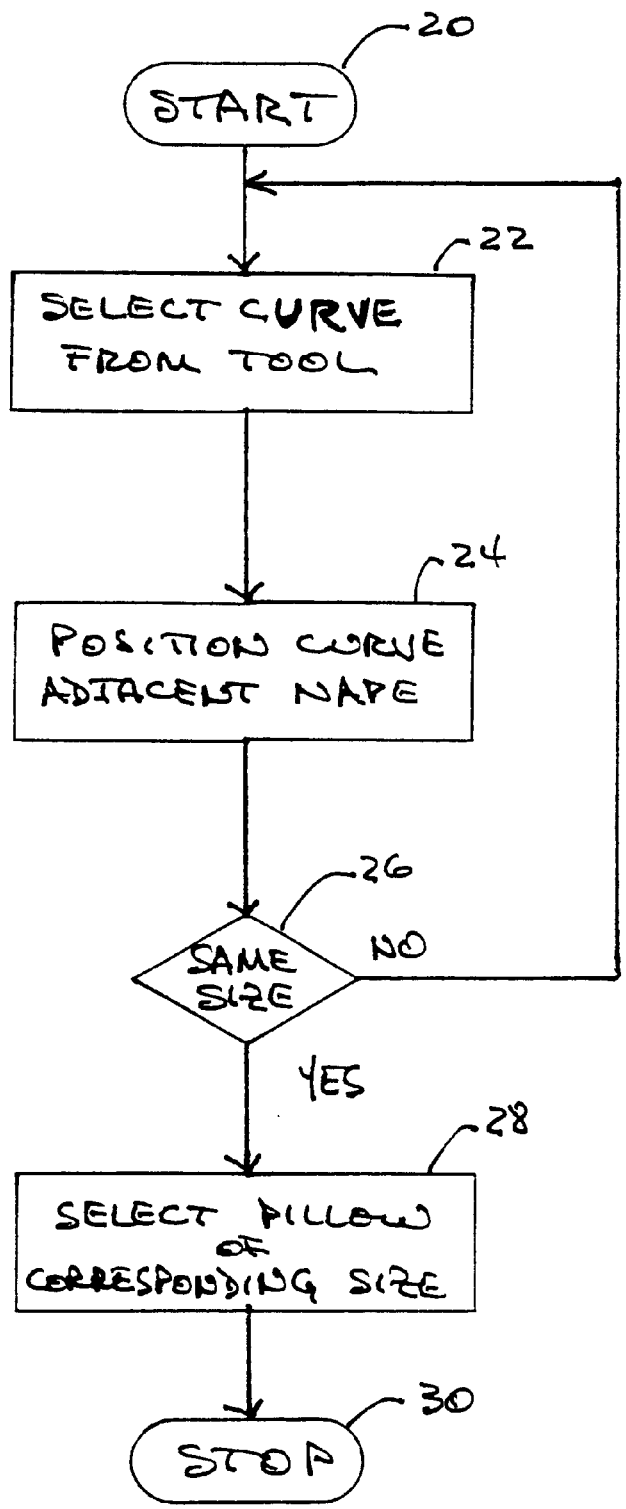
FIG. 4 is a flow diagram illustrating the method of the present invention.

As shown in FIG. 4, method aspects of the invention include measuring the cervical curve of a person and selecting a support pillow. The method starts (Block 20) by selecting a curve (Block 22) to be used, then positioning (Block 24) the complementary curve comprising predetermined dimensions adjacent the nape of the neck of the person so as to obtain a cervical curve measurement (Block 26).

Additionally included in the invention is a method for selecting (Block 28) a cervical support pillow appropriately dimensioned for a person. The method comprises the steps of measuring the cervical curve (Block 26) of a person, and selecting (Block 28) a cervical support pillow having dimensions substantially corresponding to the cervical curve measurement, so that the pillow substantially supports the neck when the person is lying down. The measurement is preferably made by positioning (Block 24) a complementary curve comprising predetermined dimensions adjacent the nape of the neck of the person so as to obtain the cervical curve measurement (Block 26).

Figure 2:
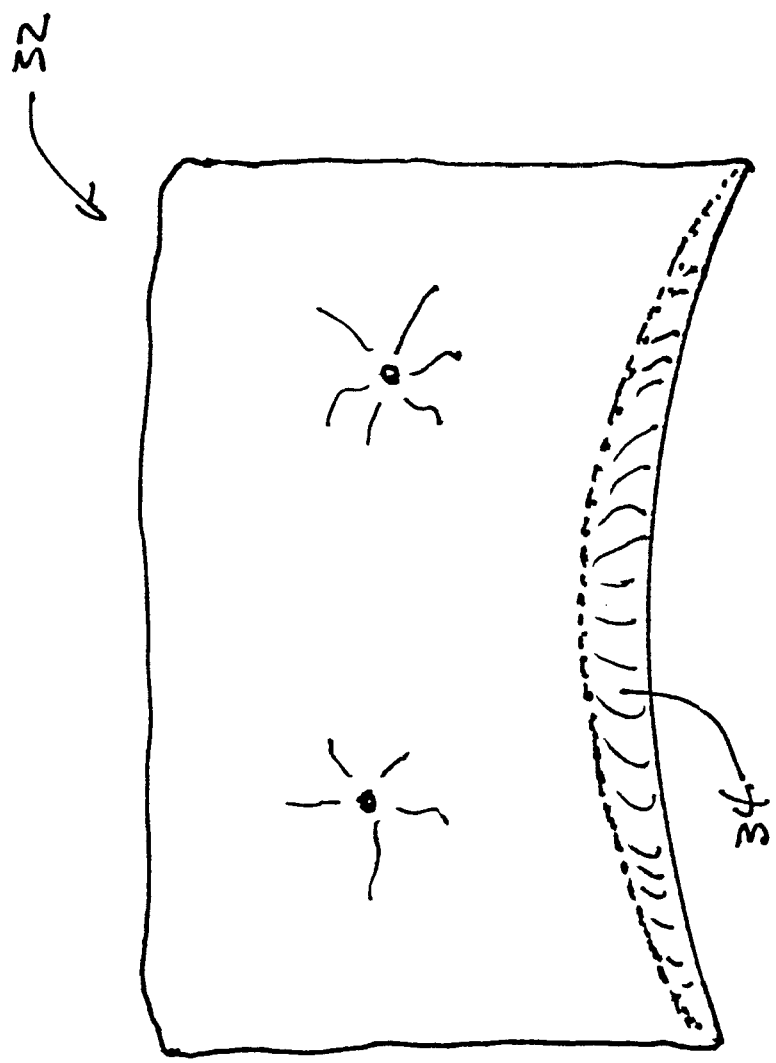
FIG. 2 is a top plan view of a cervical support pillow for use with the tool of FIG. 1.

Another method aspect of the invention includes providing the person with a cervical support pillow 32 as shown in FIG. 2. The pillow 32 has a lower portion shaped as an arcuate tube 34 substantially filled with a cushioning material, the tube defining a lower edge of the pillow and comprising a substantially tapering circumference having a diameter substantially corresponding to the measured cervical curve of the person positioned adjacent a center of the pillow and having smaller diameters positioned toward side edges of the pillow, so that the pillow aid in supporting the neck when the person is lying down.

In the drawings and specification, there have been disclosed a typical preferred embodiment of the invention, and although specific terms are employed, they are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A tool comprising a curved portion substantially complementary in shape to a cervical curve, for measuring a person's cervical curve when said curved portion is positioned adjacent the nape of the person's neck.

2. The tool of claim 1, wherein said curved portion comprises a predetermined curvature range.

3. The tool of claim 1, further comprising a plurality of curved portions.

4. The tool of claim 1, wherein said curved portion further comprises a curved edge portion of said tool.

5. A tool comprising a plurality of cards, each card including a predetermined curve substantially complementary in shape to a cervical curve, for measuring a person's cervical curve when at least one of said cards is positioned adjacent the nape of the person's neck.

6. The tool of claim 5, wherein the plurality of cards comprises a predetermined size range of curves.

7. The tool of claim 5, wherein at least one card of the plurality comprises said predetermined curve along an edge of said card.

8. A method for measuring the cervical curve of a person, comprising positioning a complementary curved tool comprising predetermined dimensions adjacent the nape of the neck of the person so as to obtain a cervical curve measurement by substantially matching the complementary curved tool to the nape of the neck.

9. A method for selecting a cervical support pillow appropriately dimensioned for a person, the method comprising the steps of:
    measuring the cervical curve of a person; and
    selecting a cervical support pillow having dimensions substantially corresponding to the cervical curve measurement so that the pillow aids in supporting the neck when the person is lying down.

10. The method of claim 9, wherein measuring is accomplished by positioning a complementary curved tool comprising predetermined dimensions adjacent nape of the neck of the person so as to obtain a cervical curve measurement.

11. A method of providing cervical support to a person lying down, the method comprising the steps of:
    measuring the cervical curve of a person; and
    providing the person with a cervical support pillow having a lower portion shaped as an arcuate tube substantially filled with a cushioning material, said tube defining a lower edge of the pillow, wherein the arcuate tube comprises a substantially tapering circumference having a diameter substantially corresponding to the measured cervical curve of the person positioned adjacent a center of the pillow, and having smaller diameters positioned toward side edges of the pillow, so that the pillow aids in supporting the neck when the person is lying down.

* * * * *